(12) United States Patent
Antalek

(10) Patent No.: US 9,237,969 B2
(45) Date of Patent: Jan. 19, 2016

(54) WOUND BARRIER PAD

(76) Inventor: Matthew D. Antalek, Getzville, NY (US)

( * ) Notice: Subject to any disclaimer, the term of this patent is extended or adjusted under 35 U.S.C. 154(b) by 575 days.

(21) Appl. No.: 13/560,126

(22) Filed: Jul. 27, 2012

(65) Prior Publication Data

US 2013/0030343 A1    Jan. 31, 2013

Related U.S. Application Data

(60) Provisional application No. 61/512,470, filed on Jul. 28, 2011.

(51) Int. Cl.
  *A61F 13/02*    (2006.01)
  *A61F 13/15*    (2006.01)

(52) U.S. Cl.
  CPC ............. *A61F 13/0216* (2013.01); *A61F 13/02* (2013.01); *A61F 2013/15024* (2013.01)

(58) Field of Classification Search
  CPC ...................................................... A61D 13/14
  USPC ....................... D24/189; 602/41–59; 128/889
  See application file for complete search history.

(56) References Cited

U.S. PATENT DOCUMENTS

| | | | |
|---|---|---|---|
| 1,736,515 A | 11/1929 | Anderson | |
| 4,468,824 A | 9/1984 | O'Hanlan | |
| 4,667,665 A * | 5/1987 | Blanco et al. | 602/47 |
| 4,779,297 A | 10/1988 | Sturges | |
| 5,048,137 A | 9/1991 | Rogers | |
| 5,062,433 A | 11/1991 | Kummer | |
| 5,086,763 A * | 2/1992 | Hathman | 602/42 |
| 5,106,629 A | 4/1992 | Cartmell et al. | |
| 5,364,339 A | 11/1994 | Carver | |
| 5,462,519 A | 10/1995 | Carver | |
| 5,562,107 A * | 10/1996 | Lavender et al. | 128/888 |
| RE35,474 E | 3/1997 | Woodard et al. | |
| 5,702,356 A * | 12/1997 | Hathman | 602/41 |
| 5,882,324 A | 3/1999 | Baranowski | |
| 5,897,516 A | 4/1999 | Kadash et al. | |
| 6,143,945 A | 11/2000 | Augustine et al. | |
| 6,211,426 B1 | 4/2001 | Abrams | |
| 6,362,387 B1 | 3/2002 | Carlson et al. | |
| 6,903,243 B1 * | 6/2005 | Burton | 602/41 |
| 6,920,881 B2 | 7/2005 | Narula et al. | |
| 6,966,088 B1 | 11/2005 | Hu | |
| 7,141,032 B2 | 11/2006 | Flam et al. | |

(Continued)

FOREIGN PATENT DOCUMENTS

| WO | WO 99/42011 | 8/1999 |
|---|---|---|
| WO | WO 03/068120 | 8/2003 |

*Primary Examiner* — Victoria J Hicks
*Assistant Examiner* — Tarla Patel
(74) *Attorney, Agent, or Firm* — Del Vecchio and Stadler LLP

(57) ABSTRACT

A wound barrier pad is provided having a housing with a housing opening. The housing has a truncated conical shape. A base plate with an opening is disposed in the housing, and the housing is filled with a fluid or padding. The wound barrier pad may also be embodied to have a cylindrical shape, a rectangular shape or other shape. The wound barrier pad may be incorporated into a garment. In another embodiment the wound barrier pad includes a ring and an adhesive such that the wound barrier pad may be directly adhered to the patient, thus eliminating the need for the garment. In another embodiment there is a wound barrier device having a pad assembly and an anti-shear member. The anti-shear member reduces frictional forces on the skin of a patient.

4 Claims, 14 Drawing Sheets

(56) References Cited

U.S. PATENT DOCUMENTS

| | | |
|---|---|---|
| 7,182,085 B1 | 2/2007 | Larsen et al. |
| 7,411,109 B2 | 8/2008 | Sigurjonsson et al. |
| 7,622,629 B2 | 11/2009 | Aali |
| 8,403,899 B2 * | 3/2013 | Sherman ........................ 604/304 |
| 8,439,860 B2 * | 5/2013 | Cali et al. ........................ 604/23 |
| 2004/0030283 A1 | 2/2004 | Brooks |
| 2005/0004500 A1 | 1/2005 | Rosser et al. |
| 2005/0060808 A1 | 3/2005 | Shaw |
| 2005/0165340 A1 | 7/2005 | Dunn et al. |
| 2006/0084902 A1 | 4/2006 | Schleicher et al. |
| 2006/0189909 A1 | 8/2006 | Hurley et al. |
| 2006/0235347 A1 | 10/2006 | Aali |
| 2007/0055205 A1 | 3/2007 | Wright et al. |
| 2007/0142761 A1 | 6/2007 | Aali |
| 2010/0030170 A1 * | 2/2010 | Keller et al. ................... 604/360 |
| 2010/0256545 A1 * | 10/2010 | Aali et al. ........................ 602/43 |
| 2010/0312159 A1 * | 12/2010 | Aali et al. ........................ 602/44 |
| 2010/0318052 A1 * | 12/2010 | Ha et al. ................... 604/385.01 |

* cited by examiner

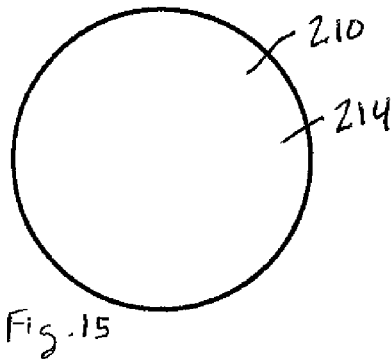
Fig. 15
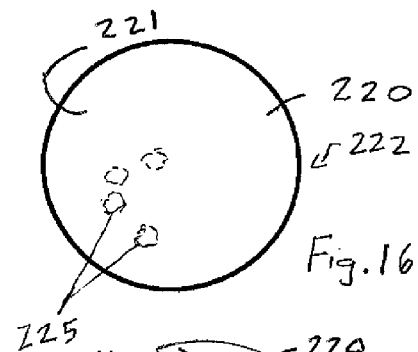
Fig. 16
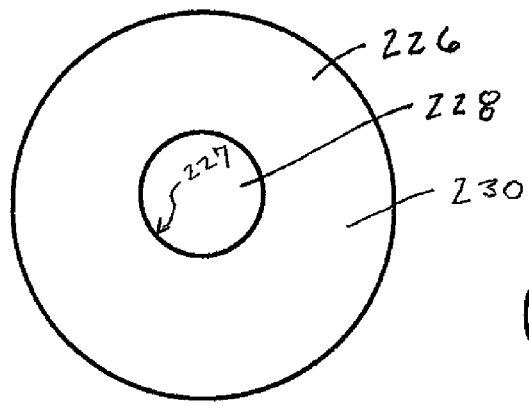
Fig. 17
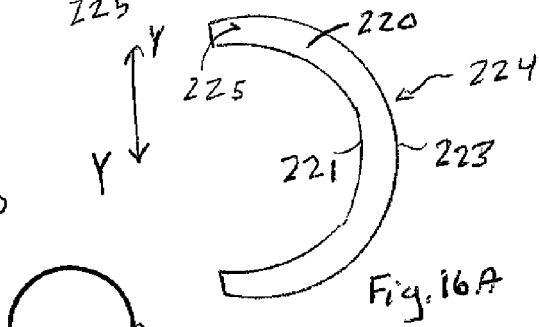
Fig. 16A
Fig. 18
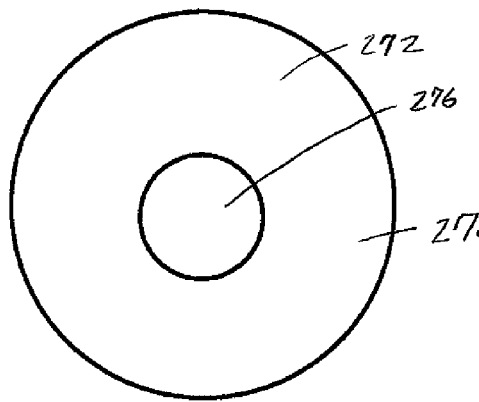
Fig. 19
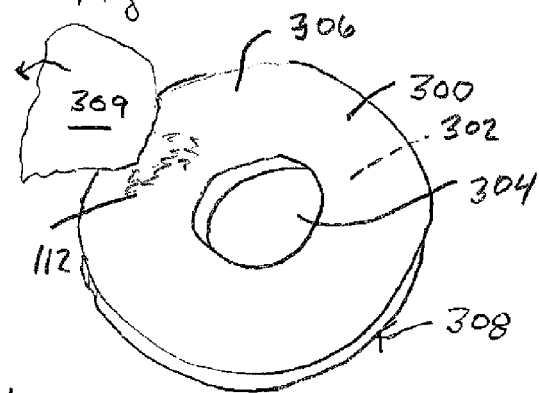
Fig. 19A
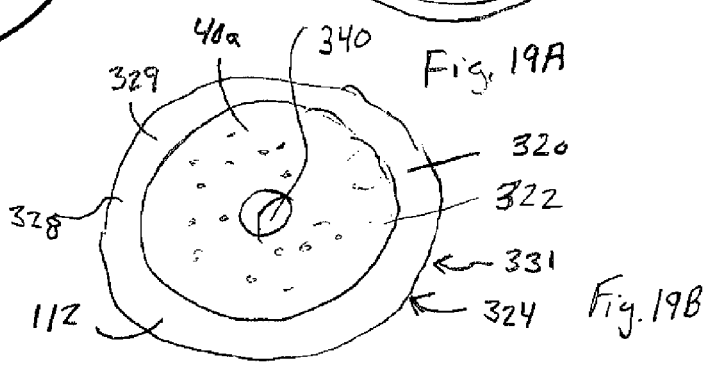
Fig. 19B

WOUND BARRIER PAD

CROSS REFERENCE TO RELATED APPLICATION

This application claims priority to U.S. Provisional Application having Ser. No. 61/512,470 filed on Jul. 28, 2011 the entire disclosure of which is hereby incorporated herein by reference.

BACKGROUND

Many patients with mobility issues have a limited ability to change positions. These individuals are at an increased risk of developing pressure ulcers, also called pressure sores or bedsores. These patients are often confined to a wheelchair or are confined to their beds for prolonged periods of time. As a result, such patients put an incredible amount of constant pressure or shear force on the same location of the body. When the same location on the body withstands constant pressure or shear force, a pressure ulcer can develop in that location. A pressure ulcer is an injury to the skin and the underlying tissues. Pressure ulcers typically develop on skin that covers bony areas of the body, such as the heel, ankles, hips, or buttocks.

Pressure ulcers are increasing in frequency among a diverse population. In particular, at risk are elderly patients with neurological abnormalities, patients with diabetes mellitus, and patients with dementia or other mental illnesses. Many of these patients are unable to move around and adjust themselves properly, so a family member, a nurse or other medical attendant is required to assist them at predetermined intervals. In some cases, the family member, the nurse or medical attendant is not available to assist with adjusting the patient's body position. Without assistance, the patient will remain in the same position increasing the likelihood of developing pressure ulcers.

There are four stages of pressure ulcers, depending on the depth of the wound and the level of tissue involvement. Stage 1 involves erythema and edema of the skin. Stage 2 involves a partial loss of skin thickness, which may include a loss of the epidermis, dermis, or both. The lesion is superficial and appears as an abrasion, blister, or shallow ulcer. Stage 3 involves a complete loss of skin thickness and includes damage or necrosis of subcutaneous tissue that may extend down to the underlying fascia. The pressure ulcer will appear as a deep crater with or without damage to the adjacent tissues. Stage 4 is the worst stage, whereby the pressure ulcer exposes the underlying tissue including tendons, bones, and ligaments.

The morbidity and mortality associated with pressure ulcers is well known. Medicare and other health insurance providers often recognize pressure ulcers as a complication of hospitalization. As such, the health insurance providers are monitoring pressure ulcer rates more closely and are increasingly less likely to reimburse the costs of treating pressure ulcers that occur in a hospital setting. Additionally, long-term care facilities and nursing homes have been scrutinized for many years at both the state and federal level, with attention to complications such as pressure ulcers.

Treatment of pressure ulcers typically includes surgical debridement, treatment with antibiotics, negative pressure dressings, and modification of the underlying skin deficit. In order for the treatment to be successful, it is paramount that the pressure and shear force on the pressure ulcer be minimized. This is typically done by repositioning the patient, using a "shifting" mattress, or by use of barrier dressings. These are also the same means used to prevent the pressure ulcer from developing. Thus, if these means weren't sufficient to prevent a pressure ulcer, they may prove ineffective at treating the pressure ulcer. As part of the treatment for pressure ulcers, it is imperative that the pressure ulcer is not subjected to pressure or shearing forces. Because of the typical location of the pressure ulcer (pelvic area, lower area, tail bone, hip), it is often extremely difficult to prevent any pressure or shear forces from being placed on the pressure ulcer. This is especially true given that it may take several months to heal a pressure ulcer.

To date, there has not been any treatment that effectively protects the pressure ulcer from pressure and shear effects.

SUMMARY

A wound barrier pad comprising a housing having opposed first and second walls, a surrounding wall extending from the first wall to the second wall, and a surrounding internal wall extending from the first wall to the second wall wherein the surrounding internal wall defines a housing opening. A housing interior is defined by the opposing first and second walls, the surrounding wall, and the surrounding internal wall. A base plate disposed in the housing and is supported on the first wall. The housing interior is filled with padding. The padding is a resilient padding, foam or can be replaced with or used in combination with a fluid.

The housing may have a truncated conical shape, a cylindrical shape, a rectangular shape or other suitable shape. An adhesive can be applied to the second wall of the housing to adhere the wound barrier pad to the patient or user.

The wound barrier pad is incorporated into a garment in one of the preferred embodiments. In use, the wound barrier pad is fitted in a pocket of the garment and positioned over the wound and bandages, such that the opening in the housing surrounds the wound. The garment holds the wound barrier pad in place such that the wound barrier pad remains in a fixed location relative to the wound.

The wound barrier pad absorbs shearing and pressure forces that are generated as the patient (or user of the wound barrier pad) moves or is moved. For example, when the patient moves while he or she is sleeping or when the patient is moved in a mechanical bed having an air mattress. This is very helpful in the treatment and prevention of wounds such as bedsores, burns and incisions.

In another preferred embodiment the wound barrier pad includes a ring with adhesive applied to the opposed sides of the ring. The adhesive may be in the form of a layer of adhesive. The adhesive joins the ring to the wound barrier pad and the patient. This embodiment eliminates the need for a garment to hold the wound barrier in place.

The wound barrier pad may have a truncated conical shape, a rectangular shape, a cylindrical shape, and may be made to have virtually as required for a particular application.

In another preferred embodiment there is a wound barrier device that includes an anti-shear pad having a pad assembly, and that includes an anti-shear member.

The pad assembly includes an outer layer, a cap, and a center member that defines a center member opening. The anti-shear member defines an anti-shear member opening. The anti-shear member is adhered to the center member of the pad assembly. A suitable wound dressing is provided and is fitted in the center member opening. The pad assembly further includes a first adhesive. The outer layer is joined to the cap with the first adhesive, and the center member and the first member are joined with the first adhesive. There is a second adhesive that joins the center member of the pad assembly with the anti-shear member, and the anti-shear member has an anti-shear member opening. The center member opening and the anti-shear member opening are axially aligned. The outer layer and the center member are made of padding in one of the preferred embodiments.

The center member opening and the anti-shear member opening define a pad passage that extends to the cap. The cap is made of a stiff resilient plastic in one of the preferred embodiments. And, the cap is movable from a relaxed cap position to a flexed cap position.

The outer layer outer layer, the cap, and the center member of the pad assembly are joined together to form the anti-shear pad, and the anti-shear pad is movable from an anti-shear pad un-flexed position to an anti-shear pad flexed position. When the pad assembly is in the flexed position the outer layer, the cap, and the center member are convex, as is the anti-shear member joined to the center member.

When the anti-shear pad is in the anti-shear pad flexed position the cap generates a biasing force that is applied to the center member. In one of the preferred embodiments when the anti-shear pad is in the anti-shear pad flexed position it is fitted in the buttocks (of a patient) such that the cap applies a force to the buttocks in order to separate the buttocks. The anti-shear member joined to the anti-shear pad abuts against the skin when the anti-shear pad is so positioned.

The wound barrier pad can be sold as a kit comprising wound barrier pads and wound barrier devices having different three-dimensional shapes.

BRIEF DESCRIPTION OF THE DRAWING FIGURES

FIG. 14A is a front view of the wound bather device when assembled.

FIG. 15 is a top plan view of an outer layer.

FIG. 16 is a top plan view of a top plan view of a cap in a relaxed cap position.

FIG. 16A is a top plan view of a top plan view of a cap in a flexed cap position.

FIG. 17 is a top plan view of a center member.

FIG. 18 is a top plan view of a dressing for a wound.

FIG. 19 is a top plan view of an anti-shear member.

FIG. 19A is a perspective view of an embodiment of an anti-shear member.

FIG. 19B is a perspective view of another embodiment of an anti-shear member.

DETAILED DESCRIPTION

It is pointed out at the outset that like reference numbers are used throughout this description to signify common elements, components, surfaces, parts and features.

Figure 1:
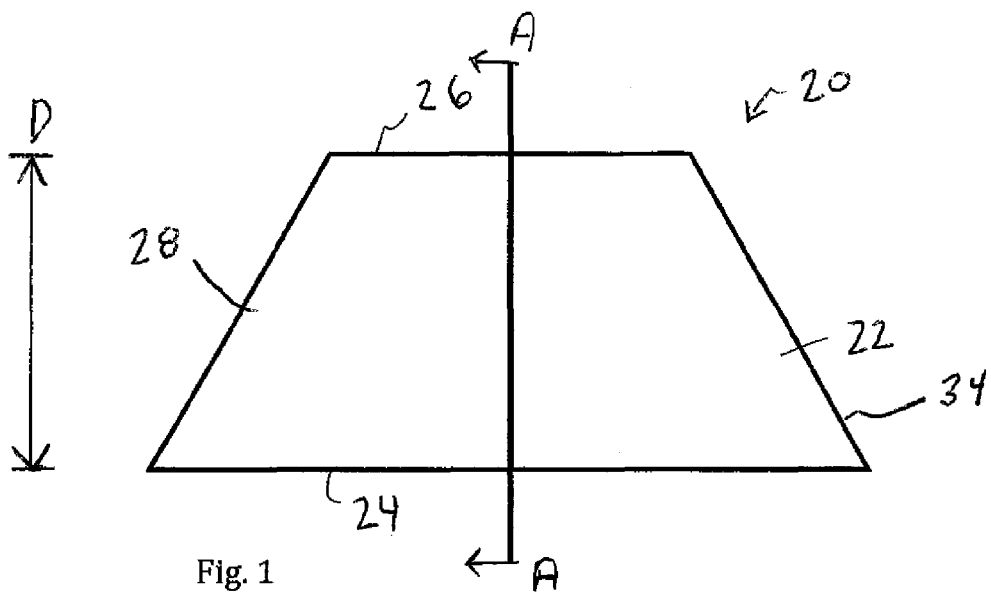
FIG. 1 is a front elevational view of a wound barrier pad.
Figure 2:
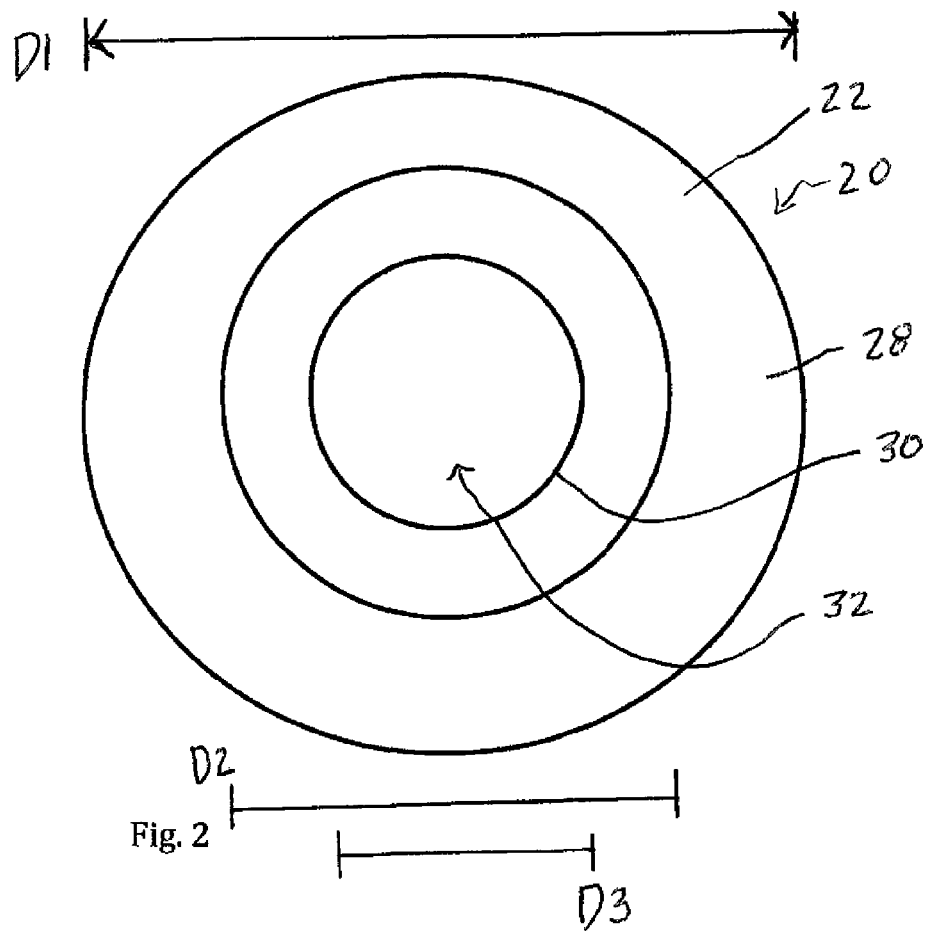
FIG. 2 is a top plan view of the wound barrier pad.
Figure 4:
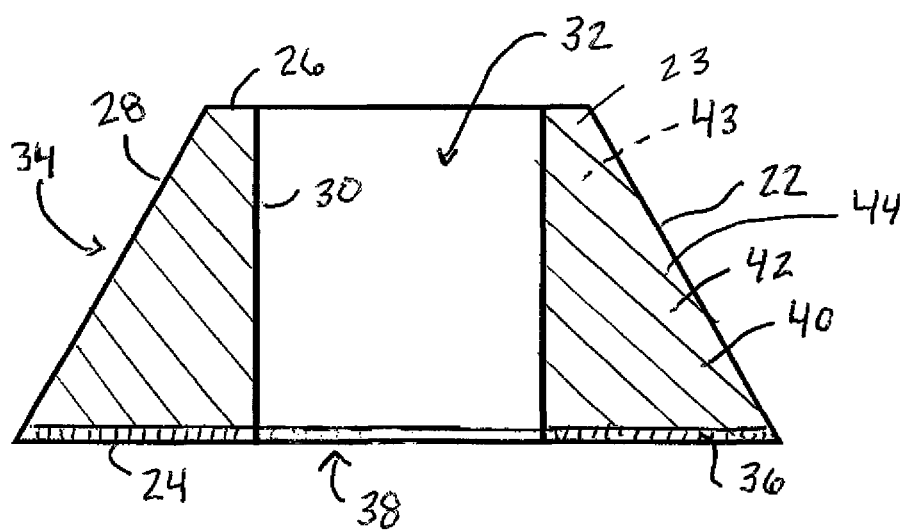
FIG. 4 is a sectional view of the wound barrier pad taken along line A-A of FIG. 1.

A wound barrier pad 20 is shown in FIGS. 1 and 2. The wound barrier pad 20 has a housing 22 having a first wall 24, an opposed second wall 26, and a surrounding exterior wall 28 that is joined to the first and second walls 24, 26. The opposed first and second walls 22, 24 are substantially flat. The housing 22 also has a surrounding internal wall 30 that is joined to the first and second walls 24, 26. As shown in FIGS. 2 and 4, the surrounding internal wall 30 defines a housing opening 32 in the housing 22. The opposed first and second walls 22, 24, the surrounding exterior wall 28 and the surrounding internal wall 30 define a housing interior 23. As shown in FIG. 2, the housing opening 32 has a housing opening diameter designated D3. The surrounding exterior and internal walls 28, 30 are each curved in one of the preferred embodiments. The housing 22 may be made of woven and nonwoven fabrics, natural or synthetic fabrics, rubber, plastics, suitable flexible materials, and combinations thereof.

The diameter of the first wall 24, designated D1 in FIG. 2, is greater than the diameter of the second wall 26, designated D2 in FIG. 2. Thus, the surrounding exterior wall 28 has a substantially truncated conical shape 34 such that the wound barrier pad 20 has a truncated conical shape. It is pointed out that a distance designated D in FIG. 1 indicates the distance from the first wall 24 to the second wall 26 may be varied to be any distance required for a particular application.

Figure 3:
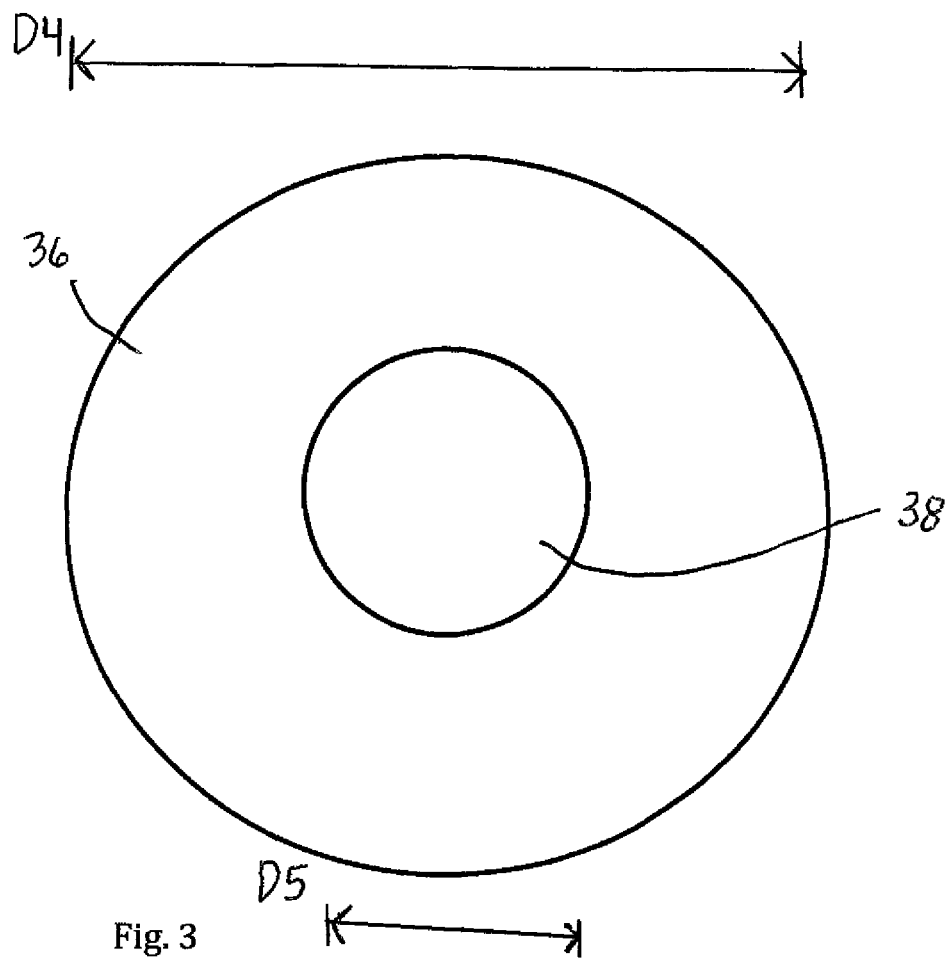
FIG. 3 is a top plan view of a base plate for use in the wound barrier pad.

As shown in FIG. 3 the wound barrier pad 20 also has a base plate 36 that is disposed in the housing interior 23 in one of the preferred embodiments. The base plate 36 is supported on the first wall 24 of the housing 22 as shown in FIG. 4 and abuts against the first wall 24 in one of the preferred embodiments. The base plate 36 has a base plate diameter designated D4 in FIG. 3 that is less that the diameter D1 of the first wall 24 of the housing 22. The base plate 36 is circular shaped and defines a base plate opening 38 having a diameter designated D5 in FIG. 3. The diameter D5 of the base plate opening 38 is less than the diameter D3 of the housing opening 32. The base plate 36 may comprise any suitable material that will not create pressure points when the patient 82 or consumer is using the wound barrier pad 20. The base plate 36 is therefore made of a flexible material, for example plastic, flexible plastic, woven fabrics, flexible fabrics, and other suitable materials.

FIG. 4 is a view taken along line A-A of FIG. 1. As shown, disposed internal to the housing 22 is padding 40. In one of the preferred embodiments, the padding 40 may be in the form of a body of padding 42 having a shape that mimics the shape of the housing 22. That is, the body of padding 42 has a truncated conical shape 44. The padding 40 may comprise resilient materials, foams, neoprene, resilient foams that return to their original shape after having been deformed, or any other suitable resilient material.

It is pointed out that the wound barrier pad 20, for example the housing 22, the padding 40 the base plate 36 can all be embodied such that they are impregnated with silver, for example silver particles which may prevent deleterious bacterial growth. The same is true for all the embodiments to be described below.

As previously mentioned, the surrounding exterior wall 28 has a substantially truncated conical shape 34. This shape provides for more even load distribution when the first wall 24 applies pressure on a patient 82 or user of the wound barrier pad 20 as will be described presently. In another preferred embodiment the padding 40 is replaced with a fluid 43. The fluid 43 can have a low viscosity in one of the preferred embodiments. The fluid 43 provides for even load distribution when the wound barrier pad 20 is in use. The fluid 43 in combination with the housing 22 behave in a manner similar to a memory pad in that the fluid 43 causes the housing 22 to return to its original truncated conical shape after having been deformed.

In other preferred embodiments, the diameter D1 of the first wall 24 is the same as the diameter D2 of the second wall 26. In such an embodiment the wound barrier pad 20 would have a substantially cylindrical shape as compared to the truncated conical shape described above.

In another preferred embodiment the above-described base plate 36 is absent.

Figure 5:
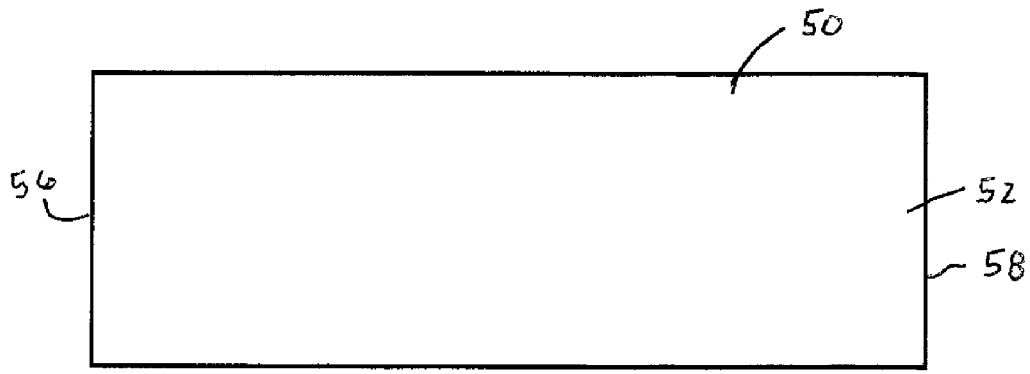
FIG. 5 is a front elevational view of a second embodiment showing a wound barrier pad wherein the wound barrier pad is rectangular shaped.
Figure 6:
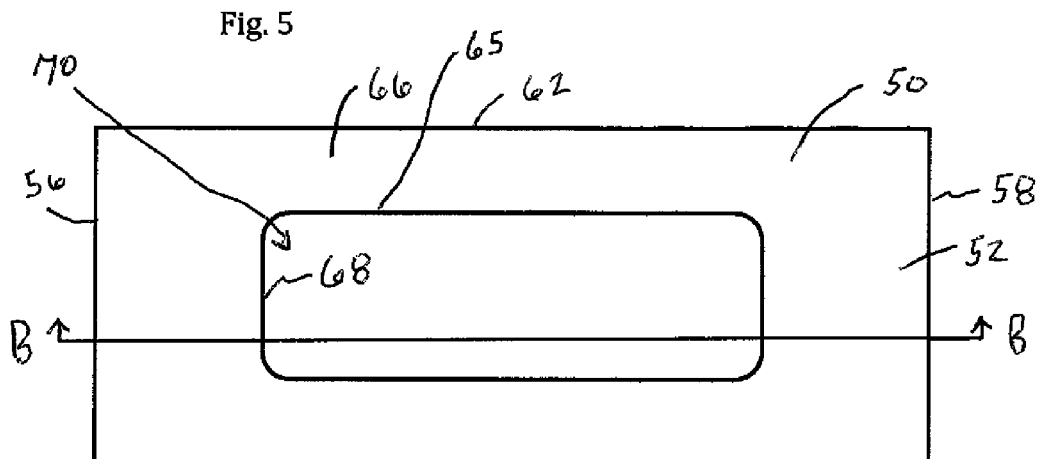
FIG. 6 is a top plan view of the second embodiment of the wound barrier pad.
Figure 7:
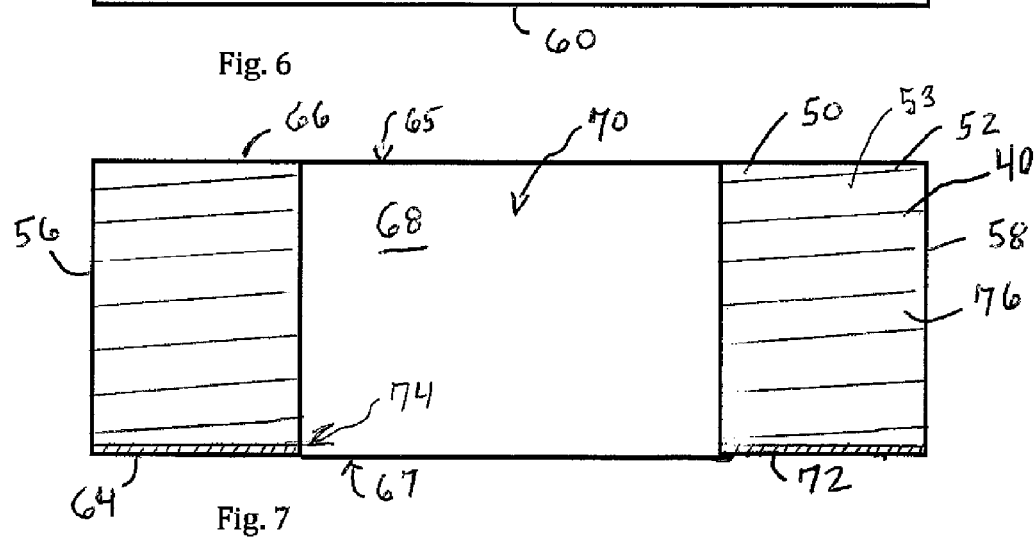
FIG. 7 is a sectional view of the rectangular shaped wound barrier pad taken along line B-B of FIG. 6.

FIGS. 5-7 show another preferred embodiment wherein a rectangular shaped wound barrier pad 50 is provided. The rectangular shaped wound barrier pad 50 has a rectangular housing 52 with opposed first and second end walls 56, 58, that are joined to a pair of opposed third and fourth end walls 60, 62. A first open wall 64 that defines a first wall opening 65 is joined to the first, second, third, and fourth end walls 56, 58, 60, 62, and an opposed second open wall 66 that defines a second wall opening 67 is joined to the first, second, third, and fourth end walls 56, 58, 60, 62. The first, second, third, and fourth end walls 56, 58, 60, 62, and the first and second open wall 64, 66 can be made of the same materials as described in connection with housing 22 described above.

The rectangular housing 52 also has a rectangular shaped internal wall 68 that is joined to the first and second open walls 64, 66. The rectangular shaped internal wall 68 defines a rectangle shaped housing opening 70 in the rectangular housing 52. The rectangular housing defines a rectangular shaped housing interior 53. As shown in FIG. 7, the rectangular shaped wound barrier pad 50 also has a rectangular shaped base plate 72 that is disposed internal to the rectangular housing 52 and is supported on the first open wall 64. The rectangular shaped base plate 72 defines a shaped base plate opening 74. The rectangular shaped base plate 72 is sized and shaped such that it is supported on the first open wall 64 and in one of the preferred embodiments abuts against the first open wall 64. The rectangular shaped base plate 72 can be made of the same materials described above in connection with the base plate 36.

FIG. 7 is a view taken along line B-B of FIG. 6. As shown, disposed internal to the rectangular housing 52 is padding 40. In one of the preferred embodiments, the padding 40 may be in the form of a rectangular body of padding 76 having a shape that mimics the shape of the rectangular housing 52 and sized so as be received therein. That is, the rectangular body of padding 76 has a shape substantially identical to the shapes shown in FIGS. 5 and 6. The padding 40 may also be in the form of the previously described fluid.

It is to be understood that while truncated conical shaped, cylindrical shaped, and rectangular shaped wound barrier pads have been described, the wound barrier pad may have virtually any geometry as required for a particular application. For example, the wound barrier pad may be triangular shaped, octagonal shaped, star shaped, ellipse shaped, and so on. All of these embodiments are within the scope of this invention.

Figure 8:
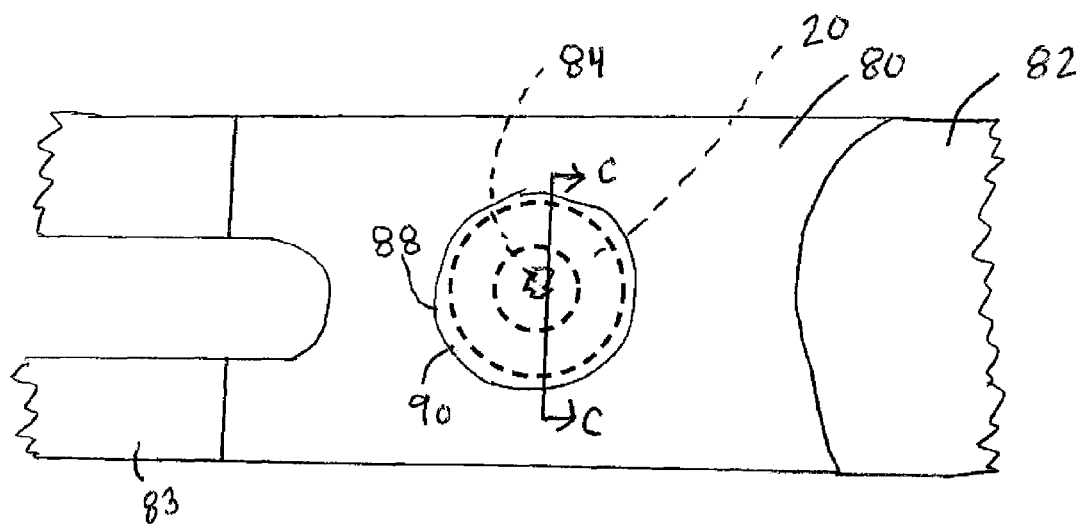
FIG. 8 is a top plan view of a garment with a wound barrier pad installed therein.
Figure 9:
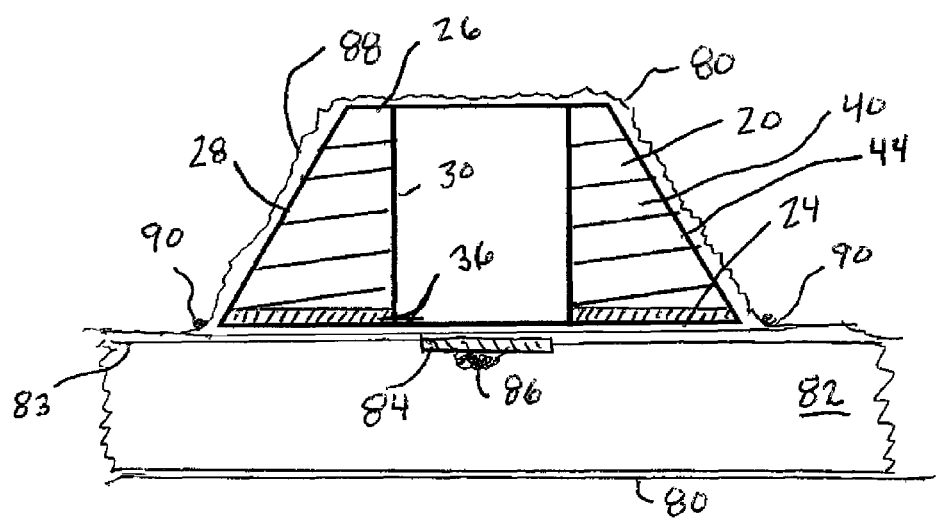
FIG. 9 is a sectional view taken along line C-C of FIG. 8 wherein the wound barrier pad is fitted in the garment.

FIGS. 8 and 9 show the wound barrier pad 20 installed in a garment 80 and being worn by a user or patient 82, with FIG. 9 being a sectional view taken along line C-C of FIG. 8. As shown, the patient 82 has a bandage or dressing 84 covering a wound 86. The dressing 84 and wound 86 are not in contact with the wound barrier pad 20. The wound may be a bedsore, a burn, a skin ulcer, a surgical incision, or other wound. The garment 80 has a pocket 88 for accommodating the wound barrier pad 20. The pocket 88 is joined to the garment 80 with a connector component 90 joined to the garment 80. The connector component 90 may be a hook and loop type fastener, a releasable adhesive or other suitable fastener so that the wound barrier pad 20 may be installed or removed for cleaning or replacement and the garment 80 can be washed and reused. In another preferred embodiment the pocket 88 is a built-in pocket and the connector component 90 may be in the form of a stitched seam. The garment 80 may be made out of a compressive elastic material, for example nylon or spandex and combinations.

One of the advantages of the wound barrier pad 20 is that it isolates the wound 86 from pressure and shearing forces that are generated by the patient 82 as he or she moves (twists, turns, rolls), for example while sleeping. The wound barrier pad 20 also protects wound 86 of the patient 82 from pressure and shearing forces while the patient 82 is being moved by his or her healthcare providers. And, the wound barrier pad 20 protects the patient 82 from pressure and shearing forces while he or she is being moved by a mechanical device, for example while resting in an inflatable bed or mattress or on a mechanical bed.

FIGS. 10-13 show another preferred embodiment wherein the wound barrier pad 20 is releaseably attached to the patient 82. The wound barrier pad 20 is structurally the same as previously described wound barrier pad 20 shown in FIGS. 1-4.

Figure 11:
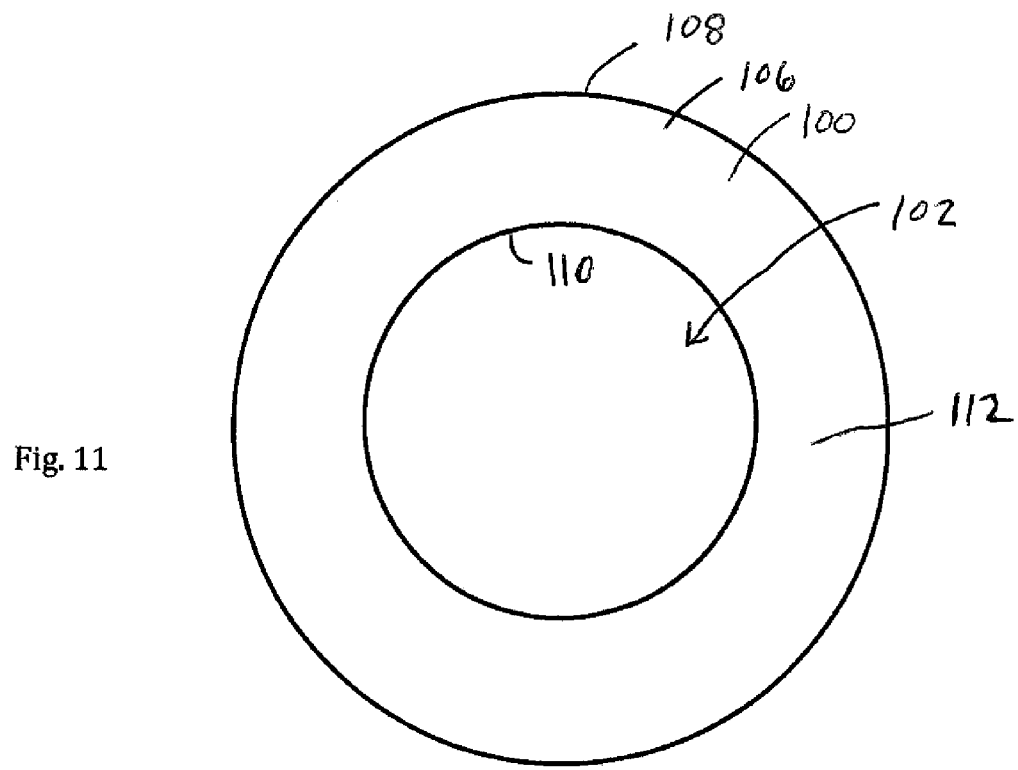
FIG. 11 is a top plan view of the ring.

As shown in FIG. 11, a ring 100 that defines a ring opening 102 is provided. The ring opening 102 has a diameter that is substantially the same as the housing opening diameter D3. The ring 100 is made of silicone in one of the preferred embodiments. The ring 100 has opposed first and second ring sides 104, 106, an outer edge 108 and an inner edge 110. The inner edge 110 defines the ring opening 102. The first and second ring sides 104, 106 each have an adhesive 112 disposed thereon, and the adhesive may be in the form of a layer of adhesive 114 in one of the preferred embodiments. The ring 102 may be cut from a commercially available sheet of silicone and coated with a suitable medical grade adhesive 112. The use of silicone sheets and suitable adhesives for use in connection with silicone sheets is well known to those having ordinary skill in the art and is therefore not described in greater detail herein.

Figure 10:
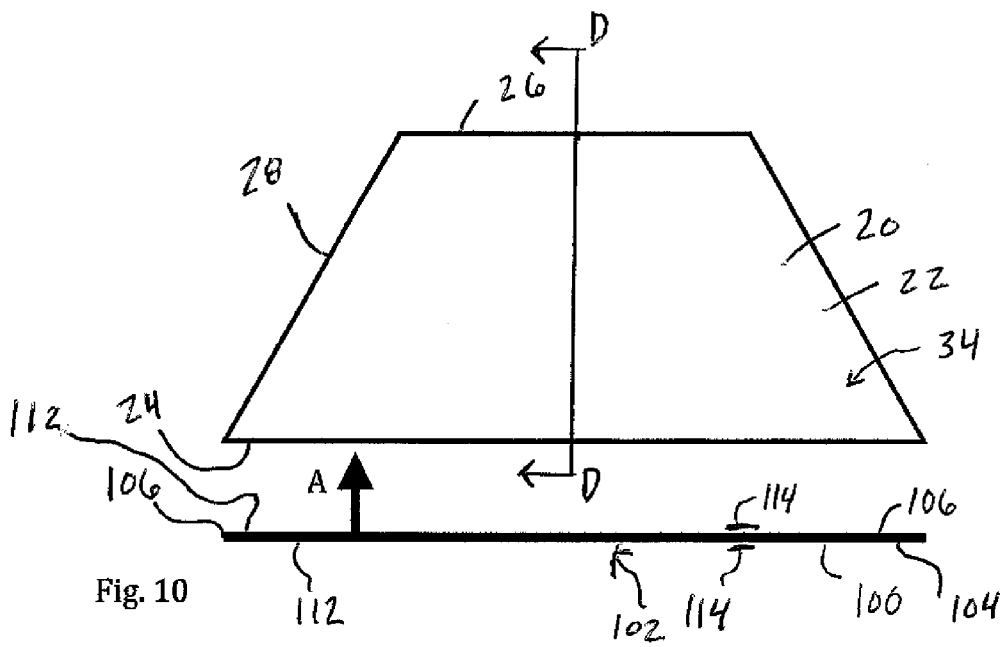
FIG. 10 is a front elevational view of a wound barrier pad and a ring that is moved into contact with the wound barrier pad as indicated by the arrow designated A.
Figure 12:
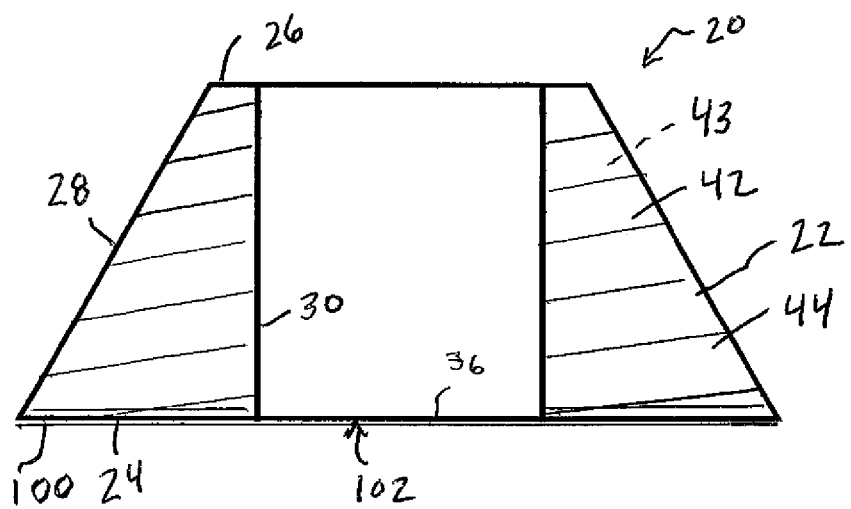
FIG. 12 is a sectional view of the wound barrier pad and the ring taken along line D-D of FIG. 10 after the ring has been joined to the wound barrier pad.
Figure 13:
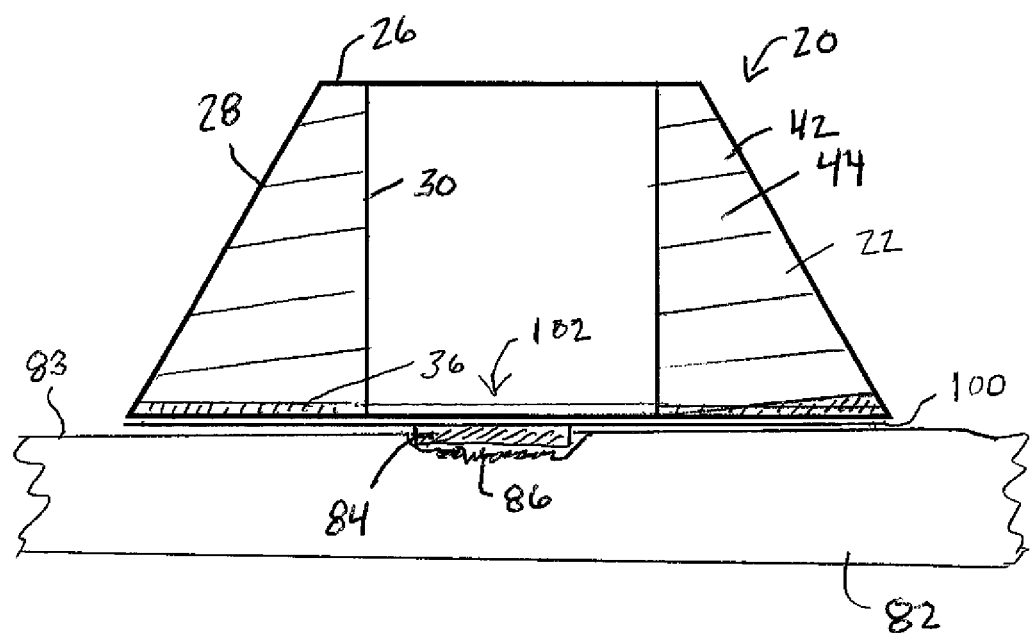
FIG. 13 is a sectional view of the wound barrier and ring adhered to a patient.

As shown in FIG. 10, the ring 100 is moved in the direction of the arrow designated A and adhered to the first wall 24 of the wound barrier pad 20. FIG. 12 is a sectional view taken along line D-D of FIG. 10 showing the ring 100 after it has been adhered to the wound barrier pad 20. FIG. 13 shows a sectional view of the wound barrier pad 20 and ring 100 after having been adhered to a patient 82. The wound barrier pad 20 isolates the wound 86 from pressure and shearing forces that are generated by the patient 82 as he or she moves (twists, turns, rolls), for example while sleeping. The wound barrier pad 20 also protects the patient 82 from pressure and shearing forces when being moved by healthcare providers. And, the wound barrier pad 20 protects the patient 82 from pressure and shearing forces while he or she is being moved by a mechanical device, for example while resting in an inflatable bed or mattress.

It is pointed out that in another preferred embodiment the ring 100 may be eliminated and the adhesive 112 may be directly applied to the first wall 24 of the wound barrier pad 20 and adhered to the patient.

In another preferred embodiment shown in FIGS. 14-24 and 26 there is a wound barrier device 199 that includes an anti-shear pad 200 having a pad assembly 202, and includes an anti-shear member 270. The wound barrier device 199 is, in one of the preferred embodiments, used for padding and protecting the skin 83 of the patient 82, for example, the skin that overlies the sacral bone of the patient 82 (see FIG. 25), it being understood that the wound barrier device 199 is capable of being used in other applications. A minimal amount of body tissue, and thus natural cushioning, exists between the sacral bone and the skin 83 that overlies the sacral bone. Coupled with the great pressures to which the skin 83 overlying the sacral bone is exposed makes this skin 83 subject to serious ulcer based wounds 86. In addition, the buttocks 85 of the patient 82 also make it quite difficult to effectively treat wounds 86 that form in the skin overlying the sacral bone because of the deep recess formed by the buttocks 85. Indeed, when just a standard commercially available bandage is applied over a wound 86 in the skin overlying the sacral bone and between the buttocks 85, the standard bandage can and will have a deleterious effect on the wound 86 due to the significant frictional forces the standard bandage imparts in the vicinity of the ulcer or wound 86.

Figure 14:
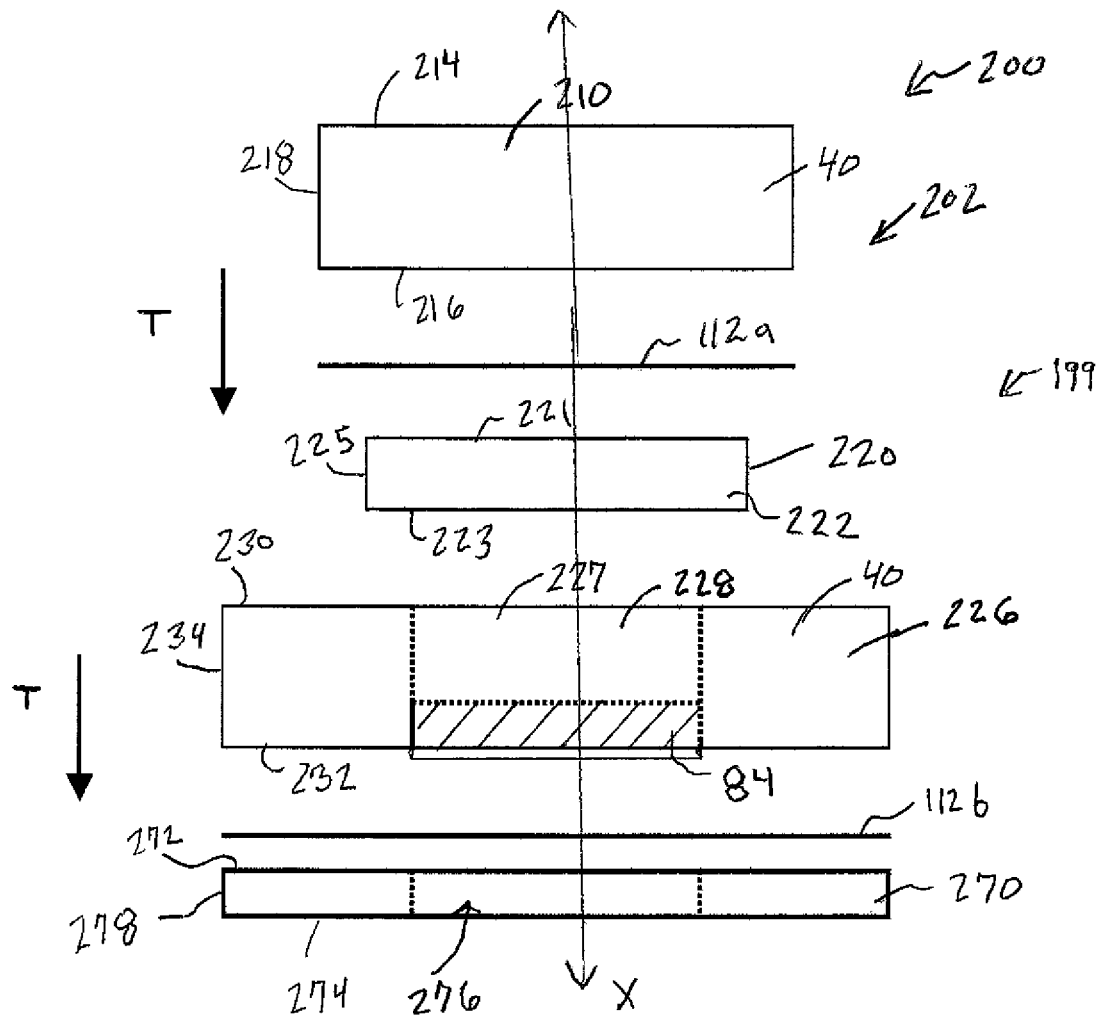
FIG. 14 is an exploded view of another embodiment showing a wound barrier device.
Figure 14:
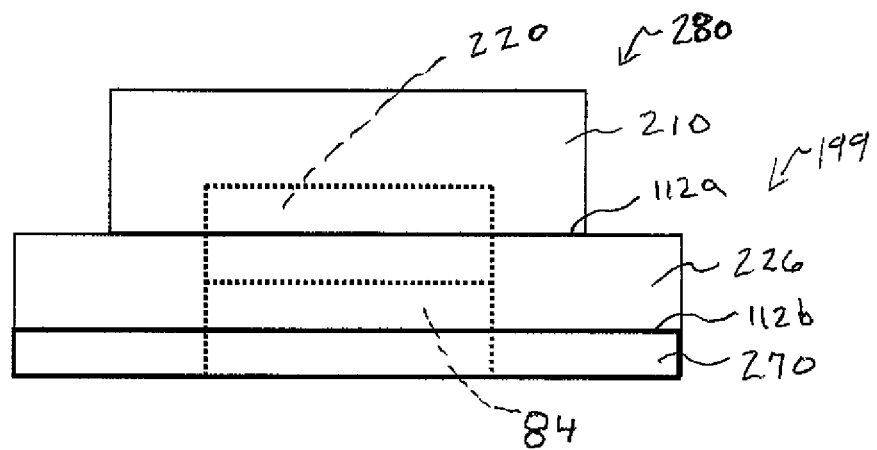

Turning now to the exploded view of FIG. 14, shown therein is a wound barrier device 199 that includes an anti-shear pad 200 having a pad assembly 202, and includes an anti-shear pad 270. FIG. 14A shows the assembled wound barrier device 199.

The pad assembly 202 has a layered structure and includes an outer layer 210 that has opposed first and second outer layer surfaces 214, 216 spaced from one another by a surrounding surface 218. In one of the preferred embodiments the outer layer 210 is made of the above described padding 40 that comprises resilient materials, foams, neoprene, resilient foams that return to their original shape after having been deformed, or any other suitable resilient material. Again, the padding can be impregnated with silver. The shape of the outer layer 210 is cylindrical as shown in FIG. 15 and can be embodied to have other shapes in other preferred embodiments.

The pad assembly 202 of the anti-shear pad 200 also includes a cap 220 and the cap 220 is resiliently deformable between a relaxed cap position 222 (shown in FIGS. 14 and 16) and a flexed cap position 224 (shown in FIG. 16A). The cap 220 is made of plastic in one of the preferred embodiments and the cap 220 can define perforations 225 in one of the preferred embodiments for airflow and for controlling the degree of resilience of the cap 220. The cap 220 has opposed first and second cap surfaces 221, 223 and a surrounding cap surface 225 extends from the first cap surface 221 to the second cap surface 223. The first cap surface 221 is joined to the second outer layer surface 216 of the outer layer 210 with a first adhesive 112a when the cap 220 is in the relaxed position 222. The first adhesive 112a may be directly applied in the form of a coating or a spray or may be embodied as an adhesive layer wherein the opposed sides of the adhesive layer are sticky and covered by removable non-stick cover sheets prior to use. Adhesives and cover sheets for use on adhesives are well known to those having ordinary skill in the art and are therefore not described in greater detail herein.

As shown in FIGS. 14 and 17, the pad assembly 202 of the anti-sheer pad 200 also includes a center member 226. The center member 226 has a first center member surface 230 and an opposed and second center member surface 232 that are spaced from one another by a center member surrounding surface 234. Each of the first center member surface 230 and second center member surface 232 meets with an internal surrounding surface 227, and the internal surrounding surface 227 defines a center member opening 228 in the center member 226. In one of the preferred embodiments the center member 226 is made of padding 40, and it can be impregnated with silver particles. The first adhesive 112a joins the second outer layer surface 216 of the outer layer 210 to the first center member surface 230 of the center member 226. It is pointed out that a central axis designated X in FIG. 14 extends axially through the center member opening 228.

After joining the outer layer 210 and the center member 226 the cap 220 is held against the outer layer 210 and the center member 226 and is kept in place. The center member opening 228 leads to the cap 220 in one of the preferred embodiments. In another preferred embodiment the cap 220 can be embodied to define a cap opening that is aligned with the center member opening 228.

The arrows designate T in FIG. 14 indicate the direction the above-described outer layer 210, cap 220, center member 226 and first adhesive 112a are brought together for form the pad assembly 202 of the anti-shear pad 200. It is pointed out that the cap 220 spans over the center member opening 228 and is disposed internal to the pad assembly 202.

As shown in FIGS. 14 and 18, the pad assembly 202 is capable of housing a wound dressing 84. The wound dressing 84 can be embodied as cotton, fabrics, and other suitable dressings that are well known to those having ordinary skill in the art. As shown in FIG. 14 wound dressing 84 is disposed in the center member opening 228, and in one of the preferred embodiment abuts against the internal surrounding surface 227 of the center member 226. The wound dressing 84 extends beyond the second center member surface 232 of the center member 226 so as to be able to be in proximity or close proximity to the wound 86.

FIGS. 14, 19, 19A and 19B show the anti-shear member 270 of the wound barrier device 199. The anti-shear member 270 is joined to the anti-shear pad 200. In particular, a second adhesive 112b adheres the second center member surface 232 of the center member 226 to the anti-shear member 270. The anti-shear member 270 has opposed first and second anti-shear member sides 272, 274 and a surrounding surface 278 that extends from the first anti-shear surface 272 to the second anti-shear surface 274. The anti-shear member 270 defines an anti-shear member opening 276 that is axially aligned along a central axis designated X. The anti-shear member 270 is made of a low friction plastic material.

In another preferred embodiment (FIG. 19A) the anti-shear member 270 is embodied as a flexible plastic bladder 300 made of a low friction material and filled with a fluid 302. The flexible plastic bladder 300 has a leak-proof central bladder opening 304. The second adhesive 112b joins one of the sides 306 of the flexible plastic bladder 300 to the center member 226. Alternatively, an adhesive 112 can be applied to the one side 306 of the flexible plastic bladder 300 and covered with a removable slip or cover sheet 309 that can be removed to expose an adhesive 112, in which case the second adhesive 112b may not be necessary. The other side 308 of the flexible plastic bladder 300 is for abutting against the patient 82 in a manner such that the central bladder opening 304 surrounds the wound.

In another preferred embodiment (FIG. 19B) the anti-shear member 270 is embodied as a breathable foam pad 320 having opposed first and second breathable sides 322, 324, and a breathable foam pad opening 340 is defined in the breathable foam pad 320. The opposed first and second breathable sides 322, 324 are made of a low friction plastic material having apertures 326, and a breathable foam 40a is disposed between them. The first and second breathable sides 322, 324 form a peripheral edge 328 that extends beyond and around the breathable foam 40a. One side 329 of the peripheral edge 328 may be coated with an adhesive 112 so as to be able to attach to the center member 226, in which case the second adhesive 112b may not be necessary, and the adhesive may be covered with a cover sheet 309. And, the other side 331 of the peripheral edge 238 may be coated with an adhesive 112 to secure the breathable foam pad 320 to the skin of the patient 82 that surrounds the wound 86, and this adhesive 112 may also be covered with a removable cover sheet 309.

Thus, the second anti-shear member side 274, upon contact with the skin of a patient 82, will not generate frictional forces and thus greatly reduces and/or eliminates detrimental shearing forces being applied to the wound 76.

Figure 20:
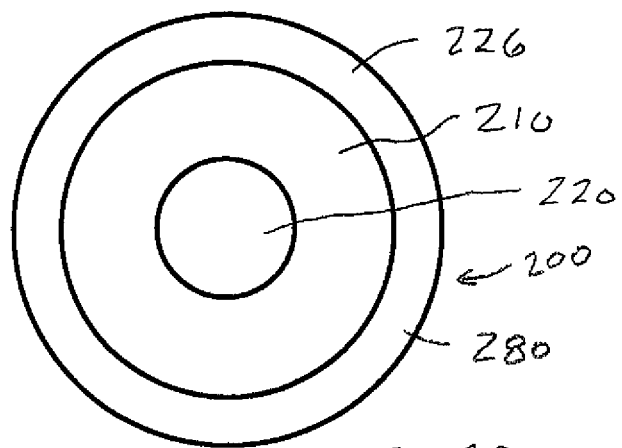
FIG. 20 is a top plan view of a pad assembly of an anti-shear pad.
Figure 21:
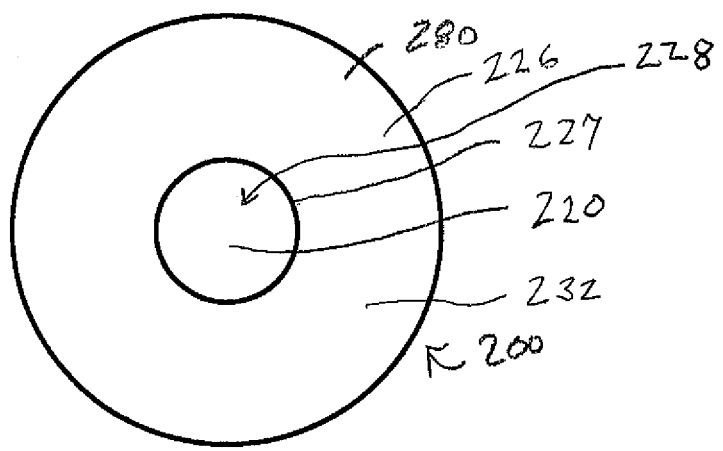
FIG. 21 is a bottom plan view of the pad assembly of the anti-shear pad.

FIG. 20 is a top plan view of the pad assembly 202 of the anti-shear pad 200 in its assembled state, and FIG. 21 is a bottom plan view of the pad assembly 202 of the anti-shear pad 200 in its assembled state.

Figure 22:
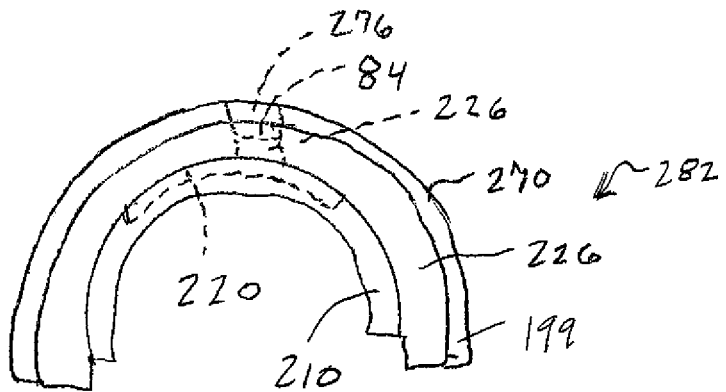
FIG. 22 is a top plan view of an anti-shear pad when in an anti-shear pad flexed position and joined to an anti-shear member.
Figures 23, 24:
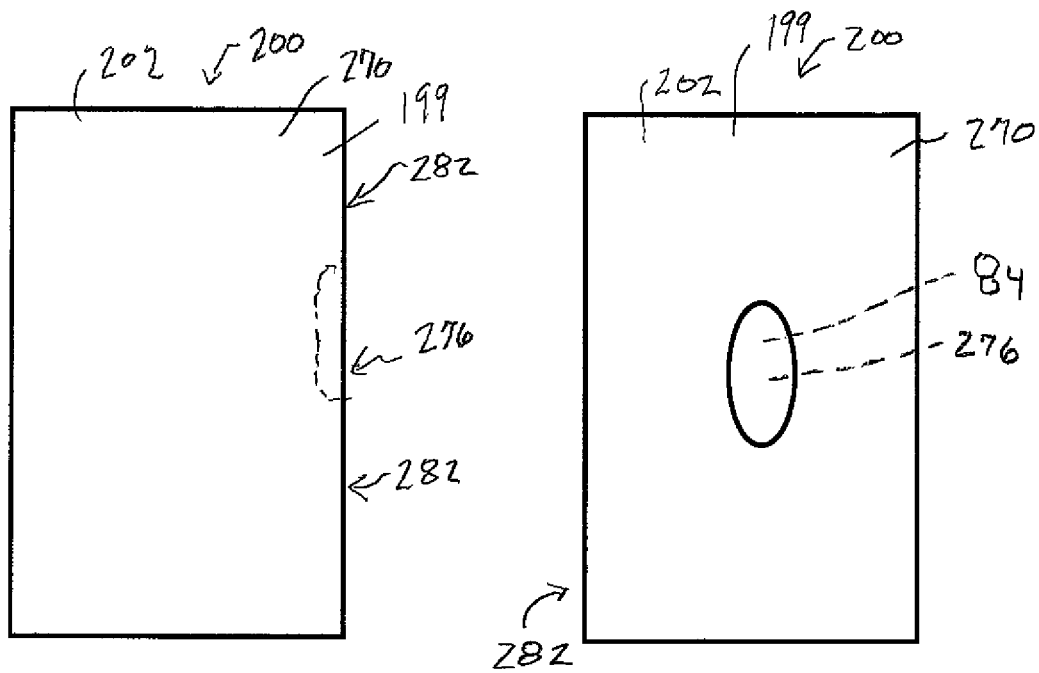
FIG. 23 is a left side elevational view of the anti-shear pad when in the anti-shear pad flexed position and joined to the anti-shear member.
FIG. 24 is a rear elevational view of the anti-shear pad when in the anti-shear pad flexed position and joined to the anti-shear member.

The anti-shear pad 200, with the anti-shear member 270 adhered thereto and with the dressing 84 housed therein, is movable from an anti-shear pad un-flexed position 280 (FIG. 14A) to an anti-shear pad flexed position 282 (FIGS. 22-24 and 26). The padding 40 from which the outer layer 210 and the center member 226 are made provides them with flexibility, and the attached anti-shear member 270 is flexible. And, the cap 220 is flexible, but it offers resistance to flexing because of the plastic from which it is made. That is, the cap 220 is stiffer than the outer layer 210, the center member 226, and the anti-shear member 270. Thus, when the anti-shear pad 200 is in the anti-shear pad flexed position 282 the cap 220 is in the flexed cap position 224, but the cap 220 biases against the outer layer 210 and the center member 226 in an attempt to return to the relaxed cap position 220. As shown in FIG. 22, when the anti-shear pad 200 is in the anti-sheer pad flexed position 282 it has a generally convex shape and the anti-shear member 270 is convex.

Figure 25:
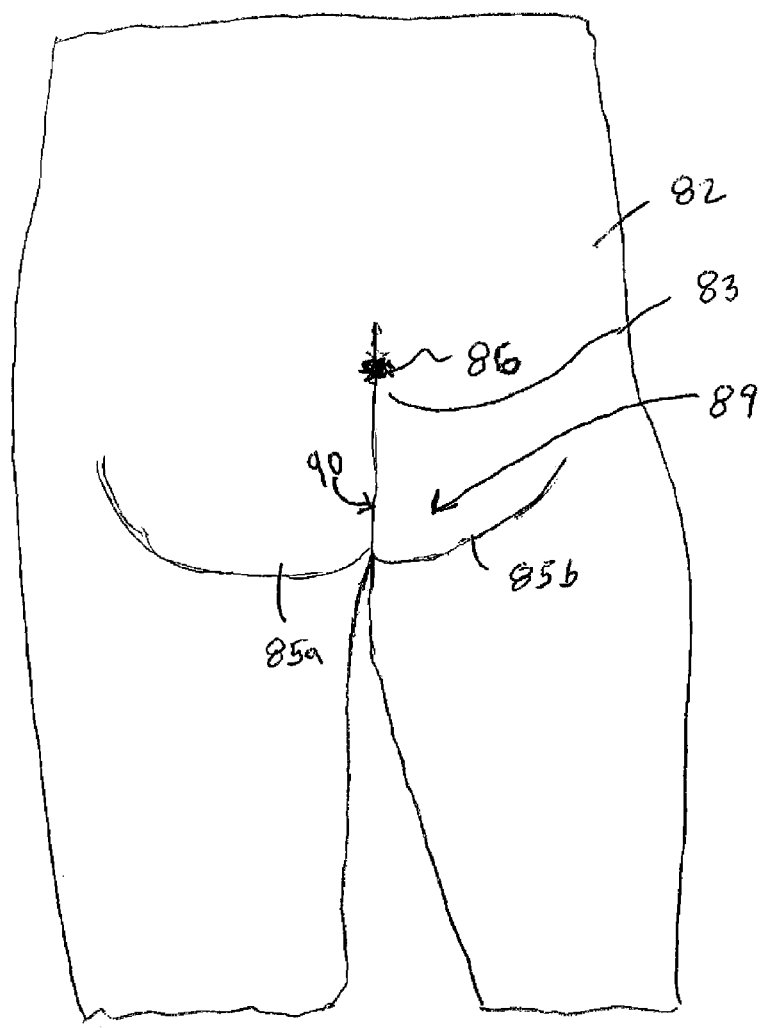
FIG. 25 is a rear view of a patient having a wound.

FIG. 25 is a rear view of a patient 82 having a wound 86, and as shown the patient has first and second buttocks 85a, 85b that form the buttocks 89 of the patient 82. The wound 86 is in the vicinity where the skin 83 of the patient 82 overlies the sacral bone.

Figure 26:
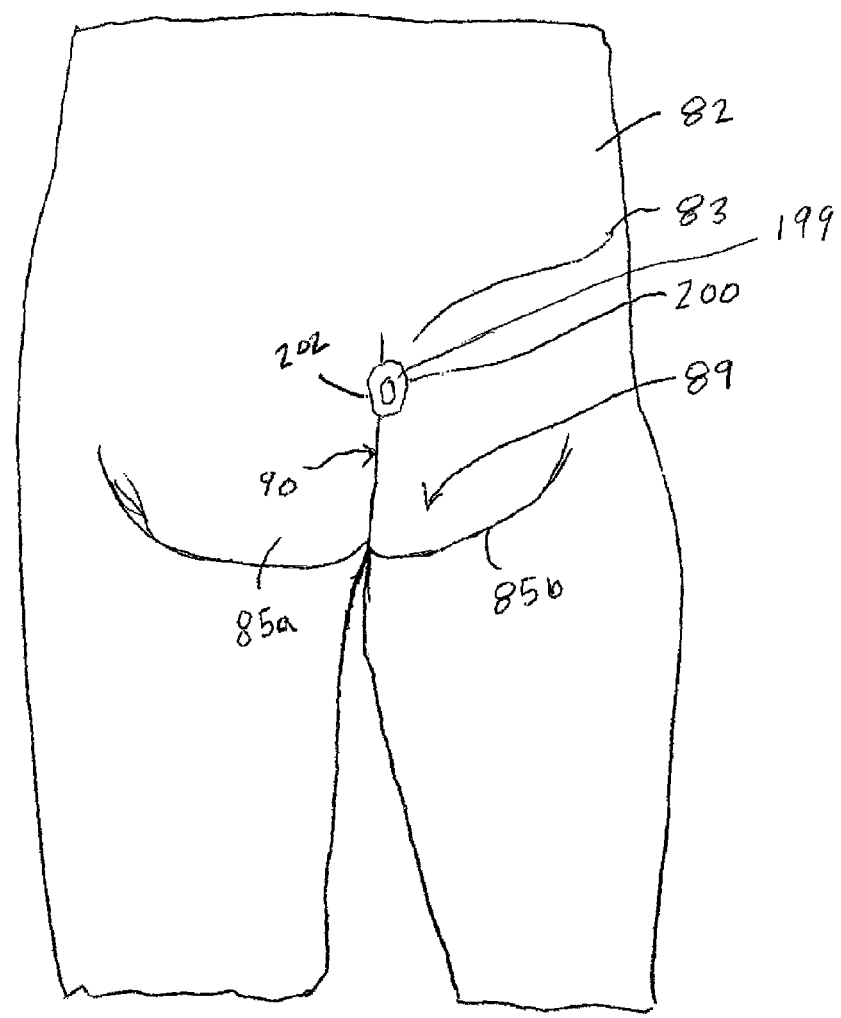
FIG. 26 is a rear view of the patient after application of the wound barrier device.

In use, the user first manually flexes the wound barrier device 199. In particular, the anti-shear pad 200 with attached anti-shear member 270 is moved into the anti-shear pad flexed position 282 and moved into a gap 90 defined by the buttocks 89, such that the anti-shear member 270 abuts against each of the first and second buttocks 85a, 85b, and such that the anti-shear member opening 276 and the dressing 84 are aligned over the wound 86. The cap 220 exerts a cap biasing force 227 (as indicated in FIG. 16A by the arrow designated Y-Y) from a position internal to the anti-shear pad 200, and the cap biasing force is transmitted through the center member 226 and the anti-shear member 270 and is applied against each of the first and second buttocks 85a, 85b, thus preventing the first and second buttocks 85a, 85b from closing together which is the natural tendency of the first and second buttocks 85a, 85b. The anti-shear member 270 is held in place by the biasing force yet at the same time allows for slippage against the skin 83 of the patient. Thus, deleterious frictional forces are not applied to the wound due to the presence of the anti-shear member 270. In addition, the first and second buttocks 85a, 85b are at all times biased apart and the wound is therefore isolated from them. And drainage from the wound 86 seeps into the dressing 84. FIG. 26 is a view showing the anti-shear pad 200 with anti-shear layer 270 after having been positioned in the buttocks 89.

Removal of frictional forces being applied to the wound 83 by use of the anti-shear pad 200 and anti-shear member 270 may significantly enhance healing time. In addition, the anti-shear pad 200 and anti-shear member 270 can be used in healthy patients that are or will be bed ridden to prevent the formation wounds 86, for example ulcers.

It is pointed out that the outer layer 210, cap 220, center member 226, and anti-shear member 270 can have virtually any geometry and are not limited to the cylindrical and rectangular shapes shown herein.

In any of the embodiments described above the padding 40 and dressing 84 can be impregnated with silver particles.

Figure 27:
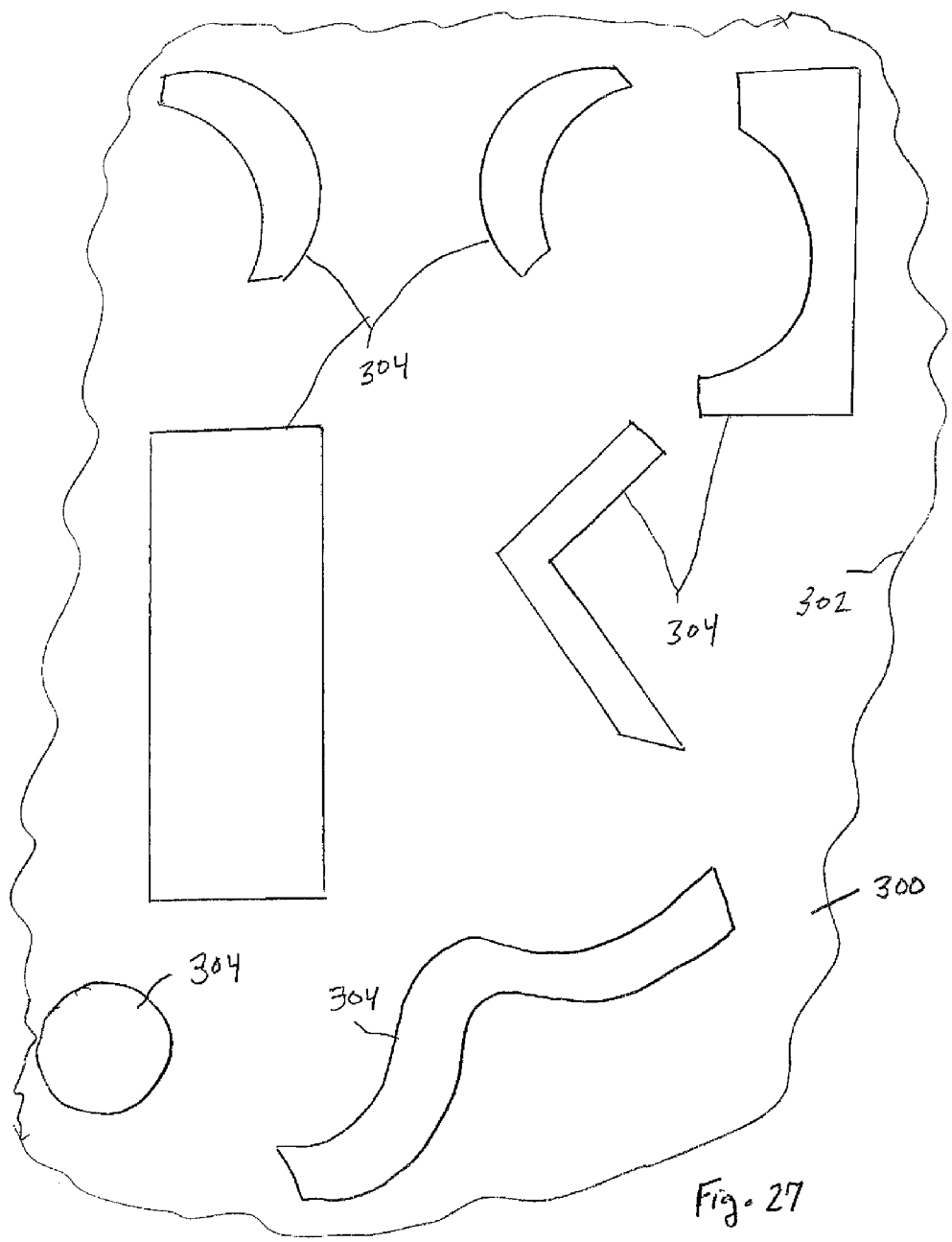
FIG. 27 is a plan view of a kit.

As shown in FIG. 27, in another preferred embodiment a kit 300 is provided (and sold) wherein the kit 300 has a kit housing 302. Disposed internal to the kit housing 302 is an assortment of wound barrier pad components 304 that are differently shaped. Indeed, the different shapes in which the wound barrier components can be embodied are virtually limitless. The internal structure and layering of the wound barrier pad components 304 can be embodied so as to be identical to the internal structure of the wound barrier pad 20 and the anti-shear pad 200. The kit may also include anti-shear members 270 wherein any adhesives 112 are covered by one of the removable cover sheets 309. The kit 300 provides the user with limitless options when treating a wound 86.

Thus the present wound barrier pad 20, the wound barrier device 199 and the embodiments described herein provide the patient 82 and the health care professional with a significantly improved ways to treat wounds, pressure ulcers and bedsores, and to prevent the onset of bedsores. The wound barrier pad 20 and wound barrier device 199 are always in a fixed location relative to the wound. This is a significant improvement over present wound treatment wherein bandages, dressing and wounds are subjected to undesirable pressure and shearing forces. In addition, the wound barrier pad 20 and the wound barrier device 199 can prevent the onset of wounds by using it at known pressure points where pressure ulcers, bedsores and other wounds commonly occur. Similarly, the wound barrier pad 20 and wound barrier device 199 may be used as soon as a healthcare provider detects the onset of a bedsore, and may be used before a wound develops or after a wound develops.

It will be appreciated by those skilled in the art that while the wound barrier pad 20 has been described in connection with particular embodiments and examples, the wound barrier pad 20 is not necessarily so limited and that other examples, uses, modifications, and departures from the embodiments, examples, and uses may be made without departing from the wound barrier pad 20. All these embodiments are intended to be within the scope and spirit of the appended claims.

What is claimed:

1. A wound barrier device comprising:
an anti-shear pad having a pad assembly, wherein the pad assembly includes:
an outer layer having opposed first and second outer layer surfaces;
a center member having opposed first and second center member surfaces and an internal surrounding surface that defines a center member opening in the center member;
a cap having opposed first and second cap surfaces;
a first adhesive;
wherein the cap is adhered to the second outer layer surface of the outer layer with the first adhesive, and the second outer layer surface is adhered to the first center member surface with the first adhesive such that the cap is held between the outer layer and center member and the cap is positioned such that the center member opening leads to the cap;
an anti-shear member and a second adhesive and wherein the second adhesive joins the second center member surface to the anti-shear member; and,
wherein the anti-shear member is a flexible bladder filled with a fluid and defines a leak-proof central bladder opening that is axially aligned with the center member opening.

2. The wound barrier device according to claim 1 wherein the outer layer and the center member are made of foam and impregnated with silver.

3. The wound barrier device according to claim 1 wherein the cap is made of a resilient material and has a relaxed cap position and a flexed cap position.

4. The wound barrier device according to claim 1 wherein the outer layer, the cap, and the center member are together movable from an anti-shear pad un-flexed position to an anti-shear pad flexed position, and when in the anti-shear pad flexed position the second outer layer surface, the second cap surface, and the second center member surface are convex.

* * * * *